United States Patent [19]

Platz

[11] Patent Number: 4,590,378

[45] Date of Patent: May 20, 1986

[54] COUNTERBALANCED RADIATION DETECTION DEVICE

[75] Inventor: Winfried Platz, Southington, Conn.

[73] Assignee: Siemens Gammasonics, Inc., Des Plaines, Ill.

[21] Appl. No.: 616,998

[22] Filed: Jun. 4, 1984

[51] Int. Cl.$^4$ ............................................. G01T 1/164
[52] U.S. Cl. .................................. 250/363 S; 378/198
[58] Field of Search ...................... 250/363 S; 378/198

[56] References Cited

U.S. PATENT DOCUMENTS

| | | | |
|---|---|---|---|
| 2,125,586 | 8/1938 | Pohl | 378/198 |
| 3,756,549 | 9/1973 | Lange | 248/123 |
| 3,767,850 | 10/1973 | McMillian et al. | 250/363 S |
| 4,216,381 | 8/1980 | Lange | 250/363 |
| 4,387,468 | 6/1983 | Fenne et al. | 378/198 |
| 4,459,485 | 7/1984 | Span | 250/363 S |

OTHER PUBLICATIONS

Handmaker et al., "Nuclear Imaging with a Mobile Gamma Camera System", Electromedica, 3/76.
Siemens brochure, "Cardiac Gamma Camera", B. V. Uithoorn, The Netherlands, 8 pages, not dated.

Primary Examiner—Carolyn E. Fields
Attorney, Agent, or Firm—Mark H. Jay

[57] ABSTRACT

A counterbalanced radiation detection device comprises a radiation detector having a specific weight. It further comprises means connected with the radiation detector and the base for positioning the radiation detector in different heights with respect to the base and it also includes electronic component means movably mounted on the base for counterbalancing the weight of the radiation detector. Furthermore, means connected with the electronic component means and the radiation detector positioning means are provided for positioning the electronic component means in different heights with respect to the base opposite to the heights of the radiation detector.

12 Claims, 2 Drawing Figures

COUNTERBALANCED RADIATION DETECTION DEVICE

BACKGROUND OF THE INVENTION

1. Field of the Invention

The invention relates to a counterbalanced radiation detection device. In particular, the invention relates to a mobile counterbalanced scintillation gamma camera.

2. Description of the Prior Art

The U.S. Pat. No. 3,756,549 (Lange) describes a counterbalanced stand for a gamma camera. An elongated frame carries a gamma camera at one end and a counterbalance weight at the opposite end. The center of gravity for various types of cameras or for cameras of varying centers of gravity may be adjusted by moving the counterweight longitudinally along the frame. This is accomplished by removing a counterweight fastener and positioning it in a selected one of support holes. The counterbalance weight is made of heavy material, such as heavy metal.

The U.S. Pat. No. 4,216,381 (Lange) illustrates a counterbalance scintillation camera for emission tomography analysis. An elongated frame carries the gamma camera at one end and a counterbalance weight at the opposite end. The elongated frame is mounted at an inner circular ring which is rotatable within a concentric outer circular ring. Again the counterweight is made of a heavy material.

Finally, the brochure "Cardiac Gamma Camera" of Siemens Gammasonics, B. V. Uithoorn, The Netherlands shows a mobile scintillation gamma camera which comprises a carriage having a base, two front wheels, a rear caster wheel and a handle connected with a base for moving the carriage. The base comprises an upright column. The radiation detector (gamma camera head) of the mobile scintillation gamma camera is tiltably and rotatably attached to the upright column of the carriage. The upright column also contains all passive electronic components, such as power supply, electronics, computer etc. A counterweight of heavy material which counterbalances the combined weights of the detector head and the upright column comprising the passive electronic components is attached to the carriage underneath the base on the opposite side of the upright column close to the rear caster wheel.

SUMMARY OF THE INVENTION

1. Objects

It is an object of this invention to provide a radiation detection device which is low in weight and which is also optimally counterbalanced.

It is another object of this invention to provide a mobile radiation detection device having low weight and being optimally counterbalanced for optimal manoeuvrability without motorizing the movement.

It is still another object of this invention to provide a mobile scintillation gamma camera which has low weight and is optimally counterbalanced for optimal manoeuvrability without motorizing the movement.

2. Summary

According to this invention a counterbalanced radiation detection device is provided, which comprises (a) a base;

(b) a radiation detector having a specific weight;

(c) means connected with the radiation detector and the base for positioning the radiation detector in different heights with respect to the base;

(d) electronic component means movably mounted on the base for counterbalancing the weight of the radiation detector; and (e) means connected with the electronic component means and the radiation detector positioning means for positioning the electronic component means in different heights with respect to the base opposite to the heights of the radiation detector.

The invention uses electronic component means of the radiation detection device (e.g., all passive electronic components outside the radiation detector, such as power supply, electronics, computer, etc.) as a counterbalance weight. No additional counterbalance weight of heavy material is necessary. Under these circumstances, a radiation detection device has been provided, which has low weight and is optimally counterbalanced by the electronic component means. In case the radiation detection device is mobile (e.g. mobile scintillation gamma camera) the low weight and the optimal counterbalance provide for optimal manoeuvrability without motorizing the movement.

In a special embodiment of the invention the radiation detection device further comprises:

(f) means connected with the radiation detector and the base for shifting the radiation detector horizontally with respect to the base; and (g) means connected with the electronic component means and the radiation detector shifting means for shifting the electronic component means horizontally with respect to the base in opposite direction to shifting of the radiation detector.

In another special embodiment of the invention (a) the radiation detector height positioning means and the radiation detector shifting means comprise a detector arm tiltably connected with the base; and (b) the means for positioning and the means for shifting the electronic component means comprise an electronic component means supporting arm tiltably connected with the base;

and the radiation detection device is further comprised of a lever mechanism for movably connecting the detector arm and the electronic component means supporting arm with each other and the base such that when tilting the detector arm together with the radiation detector in one direction the electronic component means supporting arm together with the electronic component means is tilted in the opposite direction.

In still another special embodiment the lever mechanism comprises:

(a) a fulcrum for the detector arm for turnably mounting the detector arm at the base;

(b) a fulcrum for the electronic component means supporting arm for turnably mounting the electronic component means supporting arm at the base; and (c) a connecting rod between the detector arm and the electronic component means supporting arm;

wherein the connecting rod is turnably attached to the detector arm between detector arm fulcrum and detector head and also turnably attached to the electronic component means supporting arm on one side of the fulcrum of the electronic component means supporting arm while the electronic component means is turnably attached to the electronic component means supporting arm on the other side of the fulcrum of the electronic component means supporting arm.

The foregoing and other objects, features and advantages of the invention will be apparent from the following more particular description of a preferred embodiment of the invention, as illustrated in the accompanying drawings.

DETAILED DESCRIPTION OF THE PREFERRED EMBODIMENT

Figure 1:
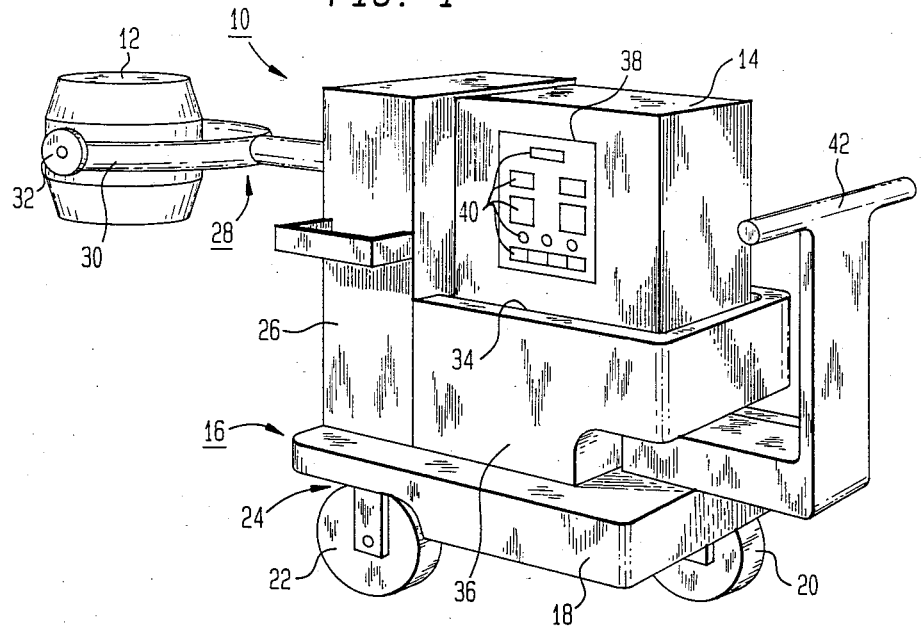
FIG. 1 is an overall perspective view of a mobile counterbalanced scintillation gamma camera according to the invention.

FIG. 1 illustrates a mobile counterbalanced scintillation gamma camera 10 comprising a radiation detector 12 (gamma camera head) having a specific weight and a housing 14 for passive electronic components (e.g. power supply, electronics, computer, etc.) having another specific weight. Both the radiation detector 12 and the housing 14 with the passive electronic components are mounted on a carriage 16.

In FIG. 1 the carriage 16 comprises a base 18 having a rear wheel 20 and two front wheels 22 and 24 (only front wheel 22 is visible in FIG. 1). The radiation detector 12 is mounted on the base 18 of the carriage 16 by means of an upright column 26 and a detector arm 28 which is tiltably attached to the upright column 26. The detector arm 28 bears the radiation detector 12 between two bifurcations of a yoke 30. The radiation detector 12 can be rotated between the bifurcations of yoke 30 around an axis 32.

The housing 14 containing the passive electronic components of the scintillation gamma camera is mounted with the inner cavity 34 of a guide member 36 mounted on the base 18. The housing 14 also comprises a control panel 38 with control elements 40 for the electronic components.

The carriage 16 also comprises a steering handle 42 connected with the rear wheel 20 for moving the carriage.

The housing 14 containing the passive electronic components serves as a counterweight for the radiation detector 12. It is connected with the detector arm 28 for being always tilted opposite to the tilting position of the detector arm 28, thus optimally counterbalancing the weight of the radiation detector 12 in each vertical and horizontal position.

Figure 2:
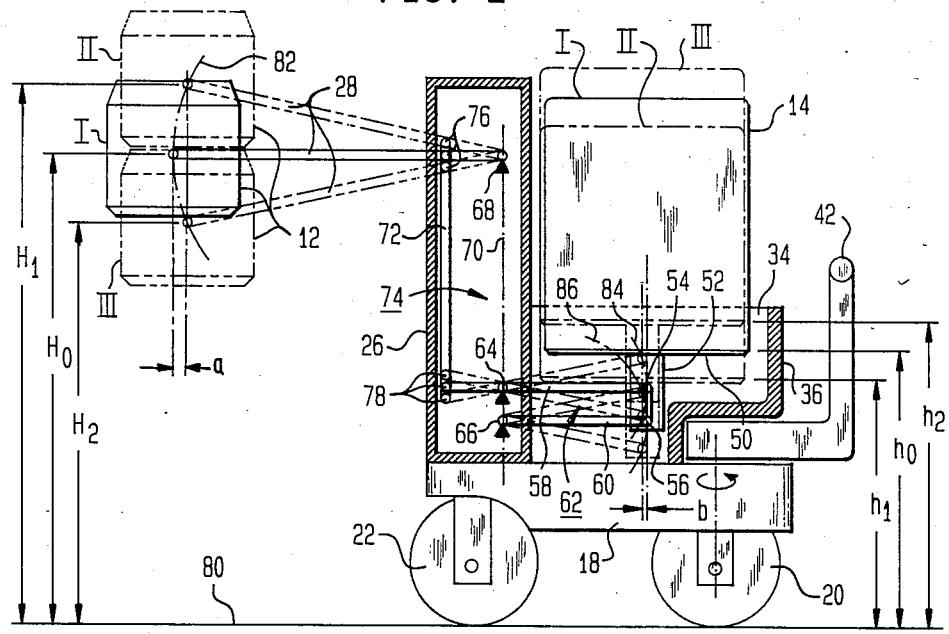
FIG. 2 is a schematic side view of the mobile counterbalanced scintillation gamma camera of FIG. 1, partially in cross section, showing a lever mechanism connection between radiation detector and electronic component means forming a counterweight with respect to the radiation detector.

For the purpose of counterbalancing in this manner, as illustrated in FIG. 2, the housing 14 containing the passive electronic components is positioned on a platform 50 which comprises a supporting member 52. The supporting member 52 comprises a first supporting arm trunnion 54 and a second supporting arm trunnion 56.

A first arm 58 is turnably connected with the first supporting arm trunnion 54 and a second arm 60 is connected with the second supporting arm trunnion 56 of the supporting member 52 of the platform 50. The first and second arms 58, 60 form together a parallelogram supporting arm 62 for the supporting member 52, the platform 50 and the housing 14 containing passive electronic components which is positioned on the platform 50.

The first arm 58 of the parallelogram supporting arm 62 is mounted on a first supporting arm fulcrum 64 which is positioned inside the upright column 26. Correspondingly, the second arm 60 of the parallelogram supporting arm 62 is mounted on a second supporting arm fulcrum 66, which is also positioned inside the upright column 26.

Also the detector arm 28, which carries the radiation detector 12 at one end, is tiltably mounted with the other end on a detector arm fulcrum 68. The detector arm fulcrum 68 is positioned inside the upright column 26 such that it lies on a vertical line 70 together with the first supporting arm fulcrum 64 and the second supporting arm fulcrum 66.

The fulcrums 64, 66 and 68 together with a connecting rod 72 for a lever mechanism 74 for movably connecting the detector arm 28 and the parallelogram supporting arm 62 for the housing 14 containing the passive electronic components of the scintillation gamma camera.

As indicated in FIG. 2 the connecting rod 72 is turnably attached with one end to detector arm 28 by means of a detector arm trunnion 76 in the depicted position between the radiation detector 12 and the detector arm fulcrum 68.

The connecting rod 72 is also turnably connected with its other end with the first arm 58 of the parallelogram supporting arm 62 by means of a third supporting arm trunnion 78, namely at that end of the first arm 58 which is opposite to the end which is turnably linked to the first supporting arm trunnion 54 of the supporting member 52 for platform 50.

The operation of the lever mechanism 74 for the purpose of counterbalancing the radiation detector by the housing 14 containing the passive electronic components is as follows:

Starting from a horizontal middle position I the detector arm 28 together with the radiation detector 12 can be tilted by the angle $+\alpha$ into position II. Also, tilting by an angle $-\alpha$ in the opposite direction into position III is possible. In the middle position I the height of axis 32 of the radiation detector 12 above floor 80 is generally designated by $H_0$. Accordingly, in position II the height is $H_1$ and in position III the height is $H_2$.

The horizontal shift of the radiation detector 12 when moving it along arc of circle 82 between positions I-II and I-III, respectively is generally designated by a.

The tilting of detector arm 28 together with radiation detector 12 is transmitted to the parallelogram supporting arm 62 by means of connecting rod 72. Due to this, the parallelogram supporting arm 62 is tilted by the angle $+\alpha$ when the radiation detector 12 is in the position III and by the angle $-\alpha$ when the radiation detector 12 is in the position II. This means that the parallelogram supporting arm 62 is always tilted in opposite direction to tilting of the detector arm 28. Only in position I of radiation detector 12 the parallelogram supporting arm 62 is in horizontal position parallel to the detector arm 28.

The afore described tilting of the parallelogram supporting arm 62 causes the platform 50 to be positioned on different heights opposite to different heights (e.g. $H_0$, $H_1$, $H_2$) of the radiation detector 12. Accordingly, the housing 14 containing the passive electronic components which is deposited on the platform 50 is also positioned in different heights. The height of the bottom of the housing 14 above floor 80 in position I of the radiation detector 12 is for example $h_0$. The heights above floor 80 in positions II and III of the radiation detector 12 are generally designated by $h_1$ and $h_2$, respectively.

Also, according to the horizontal shift a of the radiation detector 12 the platform 50 together with the housing 14 containing the passive electronic components is shifted by horizontal shift b opposite to the direction of horizontal shifting of the radiation detector 12, while the first trunnion 54 of the first arm 58 of the parallelogram supporting arm 62 is moving along arc of circle 84 and the second trunnion 56 of the second arm 60 of the parallelogram supporting arm 62 is moving along arc of circle 86.

The aforedescribed operation of lever mechanism 74 ensures that the radiation detector 12 is counterbalanced in each tilting position. This guarantees stable non-tiltable carriage support in each tilting position of the radiation detector. Furthermore, the means utilized for counterbalancing are the passive electronic components which are anyway relevant portion of the mobile scintillation gamma camera. Since no additional counterweight is necessary the weight of the mobile scintillation gamma camera is lower than that of conventional scintillation gamma cameras. The lower weight, however, ensures optimal manoeuvrability of the camera without motorizing the movement. Finally, making use of a parallelogram supporting arm for the counterweight avoids tipping over the counterweight (i.e. housing containing the passive electronic components) on the platform. Also from this point of view the scintillation gamma camera according to FIGS. 1 and 2 is safe against tipping.

Having thus described the invention with particular reference to the preferred form thereof, it will be obvious to those skilled in the art to which the invention pertains, after understanding the invention, that various changes and modifications may be made therein without departing from the spirit and scope of the invention as defined by the claims apended hereto.

What is claimed is:

1. A counterbalanced radiation detection device comprising:
   (a) a base;
   (b) a radiation detector having a known weight;
   (c) means connected with the radiation detector and the base for positioning the radiation detector in different heights with respect to the base;
   (d) electronic component means movably mounted on the base for counterbalancing the weight of the radiation detector;
   (e) means connected with the electronic component means and the radiation detector positioning means for positioning the electronic component means in different heights with respect to the base opposite to the heights of the radiation detector;
   (f) means connected with the radiation detector and the base for shifting the radiation detector horizontally with respect to the base; and
   (g) means connected with the electronic component means and the radiation detector shifting means for shifting the electronic component means horizontally with respect to the base in opposite direction to shifting of the radiation detector.

2. The radiation detection device according to claim 1, wherein
   (a) the radiation detector height positioning means and the radiation detector shifting means comprise a detector arm tiltably connected with the base; and
   (b) the means for positioning and the means for shifting the electronic component means comprise an electronic component means supporting arm tiltably connected with the base;
further comprising of lever mechanism for movably connecting the detector arm and the electronic component means supporting arm with each other and the base such that when tilting the detector arm together with the radiation detector in one direction the electronic component means supporting arm together with the electronic component means is tilted in the opposite direction.

3. The radiation device of claim 2, wherein the lever mechanism comprises:
   (a) a detector arm fulcrum pivotally securing the detector arm to the base;
   (b) a supporting arm fulcrum pivotally securing the electronic component means supporting arm to the base; and
   (c) a connecting rod between the detector arm and the electronic component means supporting arm,
the connecting rod being pivotally secured to the detector arm between the detector arm fulcrum and the detector head and also being pivotally secured to the electronic component means supporting arm on one side of the supporting arm fulcrum and the electronic component means being pivotally secured to the electronic component means supporting arm on the other side of the supporting arm fulcrum.

4. The radiation detection device according to claim 3, wherein the electronic component means supporting arm comprises a first and second arms and the supporting arm fulcrum comprises a first supporting arm fulcrum for the first arm and a second supporting arm fulcrum for the second arm and wherein both arms are linked together such as to form a parallelogram arm for supporting the electronic component means.

5. The radiation detection device according to claim 2, wherein the means for positioning and the means for shifting the electronic component means further comprising a platform for carrying the electronic component means, the platform being turnably connected with the supporting arm of the electronic component means.

6. The radiation detection device according to claim 5, wherein the electronic component means are arranged in a housing and the housing is positioned on the platform.

7. The radiation detection device according to claim 2, further comprising an upright column mounted at the base, wherein the lever mechanism is positioned in the upright column.

8. The radiation detection device according to claim 2, further comprising:
   (a) an upright column mounted at the base; and
   (b) a guide member for the electronic component means having an inner cavity;
wherein the electronic component means are arranged in the inner cavity for being shifted horizontally and vertically by means of the lever mechanism.

9. The radiation detection device according to claim 1, wherein the electronic component means are arranged in a housing and the housing together with the electronic component means counterbalance the weight of the radiation detector.

10. The radiation detection device according to claim 9, wherein the housing comprises a control panel with control elements for the electronic component means arranged in the housing.

11. The radiation detection device according to claim 1, wherein the base is part of a carriage.

12. A mobile counterbalanced scintillation gamma camera, comprising:
(a) a carriage;
(b) a radiation detector having a known weight;
(c) means connected with the radiation detector and the carriage for positioning the radiation detector in different heights with respect to the carriage;
(d) electronic component means movably mounted on the carriage for counterbalancing the weight of the radiation detector;
(e) means connected with the electronic component means and the radiation detector positioning means for positioning the electronic component means in different heights with respect to the carriage opposite to the heights of the radiation detector;
(f) means connected with the radiation detector and the carriage for shifting the radiation detector horizontally with respect to the carriage; and
(g) means connected with the electronic component means and the radiation detector shifting means for shifting the electronic component means horizontally with respect to the carriage in opposite direction to shifting of the radiation detector.

* * * * *